United States Patent
Stahmann et al.

(10) Patent No.: US 7,130,688 B2
(45) Date of Patent: *Oct. 31, 2006

(54) PACE COUNTER ISOLATION FOR CARDIAC RESYNCHRONIZATION PACING

(75) Inventors: Jeffrey E. Stahmann, Ramsey, MN (US); Rene H. Wentkowski, White Bear Lake, MN (US); Andrew P. Kramer, Stillwater, MN (US); James Kalgren, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 782 days.

This patent is subject to a terminal disclaimer.

(21) Appl. No.: 10/291,934

(22) Filed: Nov. 11, 2002

(65) Prior Publication Data

US 2003/0093123 A1    May 15, 2003

Related U.S. Application Data

(63) Continuation of application No. 09/748,798, filed on Dec. 26, 2000, now Pat. No. 6,480,742.

(51) Int. Cl.
*A61N 1/37* (2006.01)
(52) U.S. Cl. .................. 607/27; 607/9
(58) Field of Classification Search ............ None
See application file for complete search history.

(56) References Cited

U.S. PATENT DOCUMENTS

| | | | |
|---|---|---|---|
| 4,513,743 A | 4/1985 | van Arragon et al. | 128/419 |
| 4,596,255 A | 6/1986 | Snell et al. | 128/697 |
| 4,791,936 A | 12/1988 | Snell et al. | 128/697 |
| 4,809,697 A | 3/1989 | Causey, III et al. | 128/419 PT |
| 4,944,928 A | 7/1990 | Grill et al. | 423/161 |
| 5,088,488 A | 2/1992 | Markowitz et al. | 128/419 |
| 5,309,919 A | 5/1994 | Snell et al. | 128/697 |
| 5,431,691 A | 7/1995 | Snell et al. | 607/27 |
| 5,540,232 A | 7/1996 | Laney et al. | 128/697 |
| 5,549,654 A | 8/1996 | Powell | 607/32 |
| 5,620,473 A | 4/1997 | Poore | 607/27 |
| 5,622,178 A | 4/1997 | Gilham | 128/696 |
| 5,669,391 A | 9/1997 | Williams | 600/508 |
| 5,716,384 A | 2/1998 | Snell | 607/30 |
| 5,974,341 A | 10/1999 | Er et al. | 607/31 |
| 6,101,415 A | 8/2000 | Er et al. | 607/27 |
| 6,480,742 B1 * | 11/2002 | Stahmann et al. | 607/27 |

* cited by examiner

*Primary Examiner*—Kennedy Schaetzle
(74) *Attorney, Agent, or Firm*—Schwegman, Lundberg, Woessner & Kluth, P.A.

(57) ABSTRACT

A system and method recording sensing and pacing events in a cardiac rhythm management device. The method may be particularly useful in assessment of pacing parameters for ventricular resynchronization therapy.

20 Claims, 2 Drawing Sheets

| | NON-SEPARATE COUNTERS | SEPARATE COUNTERS |
|---|---|---|
| V-SENSE | 0% | 0% |
| V-PACE | 100% | -- |
| TRACKED | -- | 60% |
| TRIGGERED | -- | 0% |
| ESCAPE | -- | 40% |

|  | NON-SEPARATE COUNTERS | SEPARATE COUNTERS |
|---|---|---|
| V-SENSE | 0% | 0% |
| V-PACE | 100% | -- |
| TRACKED | -- | 0% |
| TRIGGERED | -- | 0% |
| ESCAPE | -- | 100% |

FIG. 2

|  | NON-SEPARATE COUNTERS | SEPARATE COUNTERS |
|---|---|---|
| V-SENSE | 0% | 0% |
| V-PACE | 100% | -- |
| TRACKED | -- | 60% |
| TRIGGERED | -- | 0% |
| ESCAPE | -- | 40% |

FIG. 3

|  | NON-SEPARATE COUNTERS | | SEPARATE COUNTERS | |
|---|---|---|---|---|
|  | LV | RV | LV | RV |
| V-SENSE | 40% | 60% | 40% | 60% |
| V-PACE | 60% | 85% | -- | -- |
| TRACKED | -- | -- | 0% | 0% |
| TRIGGERED | -- | -- | 45% | 60% |
| ESCAPE | -- | -- | 15% | 25% |

FIG. 4

|  | SEPARATE COUNTERS | |
|---|---|---|
|  | LV | RV |
| V-SENSE | 40% | 60% |
| V-PACE | 60% | 85% |
| TRACKED | 0% | 0% |
| TRIGGERED | 75% | 70% |
| ESCAPE | 25% | 30% |

FIG. 5

PACE COUNTER ISOLATION FOR CARDIAC RESYNCHRONIZATION PACING

CROSS-REFERENCE TO RELATED APPLICATION(S)

This application is a continuation of U.S. patent application Ser. No. 09/748,798, filed on Dec. 26, 2000, now issued as U.S. Pat. No. 6,480,742, the specification of which is incorporated by reference herein.

FIELD OF THE INVENTION

This invention pertains to methods and apparatus for cardiac rhythm management. In particular, the invention relates to methods and apparatus for providing cardiac resynchronization therapy.

BACKGROUND

Cardiac rhythm management devices are implantable devices that provide electrical stimulation to selected chambers of the heart in order to treat disorders of cardiac rhythm and include pacemakers and implantable cardioverter/defibrillators. A pacemaker is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Pacing therapy may also be applied in order to treat cardiac rhythms that are too fast, termed anti-tachycardia pacing. (As the term is used herein, a pacemaker is any cardiac rhythm management device with a pacing functionality, regardless of any other functions it may perform such as the delivery cardioversion or defibrillation shocks to terminate atrial or ventricular fibrillation.)

Also included within the concept of cardiac rhythm is the degree to which the heart chambers contract in a coordinated manner during a cardiac cycle to result in the efficient pumping of blood. The heart has specialized conduction pathways in both the atria and the ventricles that enable the rapid conduction of excitation (i.e., depolarization) throughout the myocardium. These pathways conduct excitatory impulses from the sinoatrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Patients who exhibit pathology of these conduction pathways, such as bundle branch blocks, can thus suffer compromised cardiac output.

Patients with conventional pacemakers can also have compromised cardiac output because artificial pacing with an electrode fixed into an area of the myocardium does not take advantage of the above-described specialized conduction system. The spread of excitation from a single pacing site must proceed only via the much slower conducting muscle fibers of either the atria or the ventricles, resulting in the part of the myocardium stimulated by the pacing electrode contracting well before parts of the chamber located more distally to the electrode, including the myocardium of the chamber contralateral to the pacing site. Although the pumping efficiency of the heart is somewhat reduced from the optimum, most patients can still maintain more than adequate cardiac output with artificial pacing.

Heart failure is a clinical syndrome in which an abnormality of cardiac function causes cardiac output to fall below a level adequate to meet the metabolic demand of peripheral tissues and is usually referred to as congestive heart failure (CHF) due to the accompanying venous and pulmonary congestion. CHF can be due to a variety of etiologies with ischemic heart disease being the most common. Some CHF patients suffer from some degree of AV block or are chronotropically deficient such that their cardiac output can be improved with conventional bradycardia pacing. Such pacing, however, may result in some degree of uncoordination in atrial and/or ventricular contractions due to the way in which pacing excitation is spread throughout the myocardium as described above. The resulting diminishment in cardiac output may be significant in a CHF patient whose cardiac output is already compromised. Intraventricular and/or interventricular conduction defects (e.g., bundle branch blocks) are also commonly found in CHF patients. In order to treat these problems, cardiac rhythm management devices have been developed which provide electrical pacing stimulation to one or more heart chambers in an attempt to improve the coordination of atrial and/or ventricular contractions, termed cardiac resynchronization therapy.

In order for cardiac resynchronization therapy to be effective, resynchronization pacing pulses should be delivered as often as possible. If the pacemaker is operating in a mode where pacing is inhibited by intrinsic cardiac activity, this means that a pace must be delivered before such intrinsic activation takes place. Pacemakers have various programmable pacing parameters that affect the extent to which paces are delivered and not inhibited by intrinsic beats. In order to optimally adjust these parameters, an informative record of sensing and pacing events over a period of time is needed. It is toward this general problem that the present invention is directed.

SUMMARY OF THE INVENTION

The present invention is a system and method for recording sensing and pacing events in a cardiac pacemaker that provides useful information for adjusting pacing parameters in order to optimally deliver cardiac resynchronization therapy. In accordance with the invention, paces delivered to a heart chamber occurring as a result of the expiration of different escape intervals or trigger events are separately counted. Each event that may cause a pace is assigned an isolated counter to count the number of paces that occur by reason of that event. For example, in the case of ventricular pacing, separate counters may be provided for expiration of the lower rate limit ventricular escape interval, the atrio-ventricular interval expiration in atrial-tracking ventricular pacing modes, and a ventricular sense in the case of a ventricular-triggered mode. The count of the paces due to each event may be expressed as a percentage of total cardiac cycles.

BRIEF DESCRIPTION OF THE DRAWINGS

FIGS. 2 through 5 illustrates examples of data produced by separate and non-separate pace counters.

DESCRIPTION OF THE INVENTION

Figure 1:
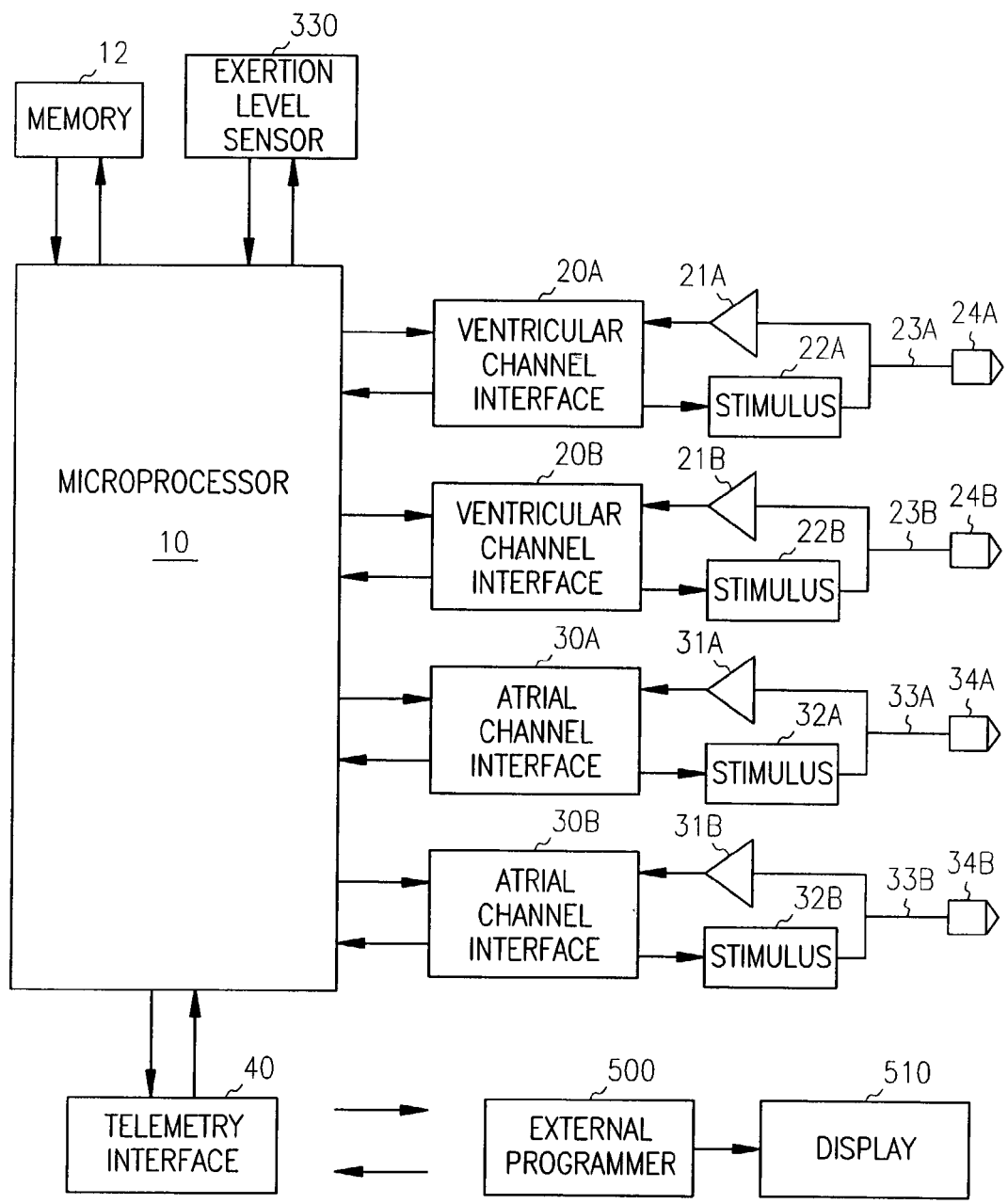
FIG. 1 is a system diagram of a pacemaker configured for biventricular pacing and sensing.

In order to properly deliver ventricular resynchronization therapy, it is important to pace the ventricles to as great an extent as possible. If the pacemaker is operating in a synchronous mode where paces are inhibited by intrinsic activity, this can be brought about by optimal adjustment of pacing parameters such as the length of escape intervals. A clinician may properly set the parameters initially, but changes in the patient's condition over time may render those parameter values inappropriate for optimally delivering resynchronization therapy. Pacemakers typically collect diagnostic data over time which can be downloaded by an external programmer using a data link. This data includes counts of senses received from sensing channels and counts of paces delivered. In order to optimally configure the pacemaker for delivering resynchronization therapy, however, more information than that is needed. Specifically, information is needed that enables a clinician to determine the reasons why paces are or are not being delivered. The present invention provides this by separately counting pacing events using isolated pace counters.

1. Hardware Platform

Pacemakers are typically implanted subcutaneously and have leads threaded intravenously into the heart to connect the device to electrodes used for sensing and pacing. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

FIG. 1 shows a system diagram of a microprocessor-based pacemaker physically configured with sensing and pacing channels for both atria and both ventricles. The controller 10 of the pacemaker is a microprocessor which communicates with a memory 12 via a bidirectional data bus. The memory 12 typically comprises a ROM (read-only memory) for program storage and a RAM (random-access memory) for data storage. The pacemaker has atrial sensing and pacing channels comprising electrode 34a–b, leads 33a–b, sensing amplifiers 31a–b, pulse generators 32a–b, and atrial channel interfaces 30a–b which communicate bidirectionally with microprocessor 10. The device also has ventricular sensing and pacing channels for both ventricles comprising electrodes 24a–b, leads 23a–b, sensing amplifiers 21a–b, pulse generators 22a–b, and ventricular channel interfaces 20a–b. In the figure, "a" designates one ventricular or atrial channel and "b" designates the channel for the contralateral chamber. In this embodiment, a single electrode is used for sensing and pacing in each channel, known as a unipolar lead. Other embodiments may employ bipolar leads which include two electrodes for outputting a pacing pulse and/or sensing intrinsic activity. The channel interfaces 20a–b and 30a–b include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. An exertion level sensor 330 (e.g., an accelerometer or a minute ventilation sensor) enables the controller to adapt the pacing rate in accordance with changes in the patient's physical activity. A telemetry interface 40 is also provided for communicating with an external programmer 500 which has an associated display 510. A pacemaker incorporating the present invention may possess all of the components in FIG. 1 and be programmable so as to operate in a number of different modes, or it may have only those components necessary to operate in a particular mode.

The controller 10 controls the overall operation of the device in accordance with programmed instructions stored in memory. The controller 10 controls the delivery of paces via the pacing channels, interprets sense signals from the sensing channels, implements timers for defining escape intervals and sensory refractory periods, and performs the pace counting functions as described below. It should be appreciated, however, that these functions could also be performed by custom logic circuitry either in addition to or instead of a programmed microprocessor.

2. Bradycardia Pacing Modes

Bradycardia pacing modes refer to pacing algorithms used to pace the atria and/or ventricles when the intrinsic atrial and/or ventricular rate is inadequate due to, for example, AV conduction blocks or sinus node dysfunction. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modem pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate limit interval is then the sum of the atrial escape interval and the atrio-ventricular interval.

Another type of synchronous pacing is atrial-triggered or ventricular-triggered pacing. In this mode, an atrium or ventricle is paced immediately after an intrinsic beat is detected in the respective chamber. Triggered pacing of a heart chamber is normally combined with inhibited demand pacing so that a pace is also delivered upon expiration of an escape interval in which no intrinsic beat occurs. Such triggered pacing may be employed as a safer alternative to asynchronous pacing when, due to far-field sensing of electromagnetic interference from external sources or skeletal muscle, false inhibition of pacing pulses is a problem. If a sense in the chamber's sensing channel is an actual depolarization and not a far-field sense, the triggered pace is delivered during the chamber's physiological refractory period and is of no consequence.

Finally, rate-adaptive algorithms may be used in conjunction with bradycardia pacing modes. Rate-adaptive pacemakers modulate the ventricular and/or atrial escape intervals based upon measurements corresponding to physical activity. Such pacemakers are applicable to situations in which atrial tracking modes cannot be used. In a rate-adaptive pacemaker, for example, the LRL is adjusted in accordance with exertion level measurements such as from an accelerometer or minute ventilation sensor in order for the heart rate to more nearly match metabolic demand. The adjusted LRL is then termed the sensor-indicated rate.

3. Cardiac Resynchronization Therapy

Cardiac resynchronization therapy is pacing stimulation applied to one or more heart chambers in a manner that restores or maintains synchronized bilateral contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. In that sense, conventional bradycardia pacing of an atrium and/or a ventricle may be considered as resynchronization therapy. Resynchronization pacing, however, may also involve pacing both ventricles and/or both atria in accordance with a synchronized pacing mode as described below. A single chamber may also be resynchronized to compensate for intra-atrial or intra-ventricular conduction delays by delivering paces to multiple sites of the chamber.

It is advantageous to deliver resynchronization therapy in conjunction with one or more synchronous bradycardia pacing modes, such as are described above. One atrial and/or one ventricular pacing sites are designated as rate sites, and paces are delivered to the rate sites based upon pacing and sensed intrinsic activity at the site in accordance with the bradycardia pacing mode. In a single-chamber bradycardia pacing mode, for example, one of the paired atria or one of the ventricles is designated as the rate chamber. In a dual-chamber bradycardia pacing mode, either the right or left atrium is selected as the atrial rate chamber and either the right or left ventricle is selected as the ventricular rate chamber. The heart rate and the escape intervals for the pacing mode are defined by intervals between sensed and paced events in the rate chambers only. Resynchronization therapy may then be implemented by adding synchronized pacing to the bradycardia pacing mode where paces are delivered to one or more synchronized pacing sites in a defined time relation to one or more selected sensing and pacing events that either reset escape intervals or trigger paces in the bradycardia pacing mode. Multiple synchronized sites may be paced through multiple synchronized sensing/pacing channels, and the multiple synchronized sites may be in the same or different chambers as the rate site.

In bilateral synchronized pacing, which may be either biatrial or biventricular synchronized pacing, the heart chamber contralateral to the rate chamber is designated as a synchronized chamber. For example, the right ventricle may be designated as the rate ventricle and the left ventricle designated as the synchronized ventricle, and the paired atria may be similarly designated. Each synchronized chamber is then paced in a timed relation to a pace or sense occurring in the contralateral rate chamber.

One synchronized pacing mode may be termed offset synchronized pacing. In this mode, the synchronized chamber is paced with a positive, negative, or zero timing offset as measured from a pace delivered to its paired rate chamber, referred to as the synchronized chamber offset interval. The offset interval may be zero in order to pace both chambers simultaneously, positive in order to pace the synchronized chamber after the rate chamber, or negative to pace the synchronized chamber before the rate chamber. One example of such pacing is biventricular offset synchronized pacing where both ventricles are paced with a specified offset interval. The rate ventricle is paced in accordance with a synchronous bradycardia mode which may include atrial tracking, and the ventricular escape interval is reset with either a pace or a sense in the rate ventricle. (Resetting in this context refers to restarting the interval in the case of an LRL ventricular escape interval and to stopping the interval in the case of an AVI.) Thus, a pair of ventricular paces are delivered after expiration of the AVI escape interval or expiration of the LRL escape interval, with ventricular pacing inhibited by a sense in the rate ventricle that restarts the LRL escape interval and stops the AVI escape interval. In this mode, the pumping efficiency of the heart will be increased in some patients by simultaneous pacing of the ventricles with an offset of zero. However, it may be desirable in certain patients to pace one ventricle before the other in order to compensate for different conduction velocities in the two ventricles, and this may be accomplished by specifying a particular positive or negative ventricular offset interval.

Another synchronized mode is triggered synchronized pacing. In one type of triggered synchronized pacing, the synchronized chamber is paced after a specified trigger interval following a sense in the rate chamber, while in another type the rate chamber is paced after a specified trigger interval following a sense in the synchronized chamber. The two types may also be employed simultaneously. For example, with a trigger interval of zero, pacing of one chamber is triggered to occur in the shortest time possible after a sense in the other chamber in order to produce a coordinated contraction. (The shortest possible time for the triggered pace is limited by a sense-to-pace latency period dictated by the hardware.) This mode of pacing may be desirable when the intra-chamber conduction time is long enough that the pacemaker is able to reliably insert a pace before depolarization from one chamber reaches the other. Triggered synchronized pacing can also be combined with offset synchronized pacing such that both chambers are paced with the specified offset interval if no intrinsic activity is sensed in the rate chamber and a pace to the rate chamber is not otherwise delivered as a result of a triggering event. A specific example of this mode is ventricular triggered synchronized pacing where the rate and synchronized chambers are the right and left ventricles, respectively, and a sense in the right ventricle triggers a pace to the left ventricle and/or a sense in the left ventricle triggers a pace to the right ventricle.

As with other synchronized pacing modes, the rate chamber in a triggered synchronized pacing mode can be paced with one or more synchronous bradycardia pacing modes. If the rate chamber is controlled by a triggered bradycardia mode, a sense in the rate chamber sensing channel, in addition to triggering a pace to the synchronized chamber, also triggers an immediate rate chamber pace and resets any rate chamber escape interval. The advantage of this modal combination is that the sensed event in the rate chamber sensing channel might actually be a far-field sense from the synchronized chamber, in which case the rate chamber pace should not be inhibited. In a specific example, the right and left ventricles are the rate and synchronized chambers, respectively, and a sense in the right ventricle triggers a pace to the left ventricle. If right ventricular triggered pacing is also employed as a bradycardia mode, both ventricles are paced after a right ventricular sense has been received to allow for the possibility that the right ventricular sense was actually a far-field sense of left ventricular depolarization in the right ventricular channel. If the right ventricular sense were actually from the right ventricle, the right ventricular pace would occur during the right ventricle's physiological refractory period and cause no harm.

As mentioned above, certain patients may experience some cardiac resynchronization from the pacing of only one ventricle and/or one atrium with a conventional bradycardia pacing mode. It may be desirable, however, to pace a single atrium or ventricle in accordance with a pacing mode based upon senses from the contralateral chamber. This mode, termed synchronized chamber-only pacing, involves pacing only the synchronized chamber based upon senses from the rate chamber. One way to implement synchronized chamber-only pacing is to pseudo-pace the rate chamber whenever the synchronized chamber is paced before the rate chamber is paced, such that the pseudo-pace inhibits a rate chamber pace and resets any rate chamber escape intervals. Such pseudo-pacing can be combined with the offset synchronized pacing mode using a negative offset to pace the synchronized chamber before the rate chamber and thus pseudo-pace the rate chamber, which inhibits the real scheduled rate chamber pace and resets the rate chamber pacing escape intervals. One advantage of this combination is that sensed events in the rate chamber will inhibit the synchronized chamber-only pacing, which may benefit some patients by preventing pacing that competes with intrinsic activation (i.e., fusion beats). Another advantage of this combination is that rate chamber pacing can provide backup pacing when in a synchronized chamber-only pacing mode, such that when the synchronized chamber pace is prevented, for example to avoid pacing during the chamber vulnerable period following a prior contraction, the rate chamber will not be pseudo-paced and thus will be paced upon expiration of the rate chamber escape interval. Synchronized chamber-only pacing can be combined also with a triggered synchronized pacing mode, in particular with the type in which the synchronized chamber is triggered by a sense in the rate chamber. One advantage of this combination is that sensed events in the rate chamber will trigger the synchronized chamber-only pacing, which may benefit some patients by synchronizing the paced chamber contractions with premature contralateral intrinsic contractions.

An example of synchronized chamber-only pacing is left ventricle-only synchronized pacing where the rate and synchronized chambers are the right and left ventricles, respectively. Left ventricle-only synchronized pacing may be advantageous where the conduction velocities within the ventricles are such that pacing only the left ventricle results in a more coordinated contraction by the ventricles than with conventional right ventricular pacing or biventricular pacing. Left ventricle-only synchronized pacing may be implemented in inhibited demand modes with or without atrial tracking, similar to biventricular pacing. A left ventricular pace is then delivered upon expiration of the AVI escape interval or expiration of the LRL escape interval, with left ventricular pacing inhibited by a right ventricular sense that restarts the LRL escape interval and stops the AVI escape interval.

In the synchronized modes described above, the rate chamber is synchronously paced with a mode based upon detected intrinsic activity in the rate chamber, thus protecting the rate chamber against paces being delivered during the vulnerable period. In order to provide similar protection to a synchronized chamber or synchronized pacing site, a synchronized chamber protection period (SCPP) may be provided. (In the case of multi-site synchronized pacing, a similar synchronized site protection period may be provided for each synchronized site.) The SCPP is a programmed interval which is initiated by sense or pace occurring in the synchronized chamber during which paces to the synchronized chamber are inhibited. For example, if the right ventricle is the rate chamber and the left ventricle is the synchronized chamber, a left ventricular protection period LVPP is triggered by a left ventricular sense which inhibits a left ventricular pace which would otherwise occur before the escape interval expires. The SCPP may be adjusted dynamically as a function of heart rate and may be different depending upon whether it was initiated by a sense or a pace.

The SCPP provides a means to inhibit pacing of the synchronized chamber when a pace might be delivered during the vulnerable period or when it might compromise pumping efficiency by pacing the chamber too close to an intrinsic beat. In the case of a triggered mode where a synchronized chamber sense triggers a pace to the synchronized chamber, the pacing mode may be programmed to ignore the SCPP during the triggered pace. Alternatively, the mode may be programmed such that the SCPP starts only after a specified delay from the triggering event, which allows triggered pacing but prevents pacing during the vulnerable period.

In the case of synchronized chamber-only synchronized pacing, a synchronized chamber pace may be inhibited if a synchronized chamber sense occurs within a protection period prior to expiration of the rate chamber escape interval. Since the synchronized chamber pace is inhibited by the protection period, the rate chamber is not pseudo-paced and, if no intrinsic activity is sensed in the rate chamber, it will be paced upon expiration of the rate chamber escape intervals. The rate chamber pace in this situation may thus be termed a safety pace. For example, in left ventricle-only synchronized pacing, a right ventricular safety pace is delivered if the left ventricular pace is inhibited by the left ventricular protection period and no right ventricular sense has occurred.

As noted above, synchronized pacing may be applied to multiple sites in the same or different chambers. The synchronized pacing modes described above may be implemented in a multi-site configuration by designating one sensing/pacing channel as the rate channel for sensing/pacing a rate site, and designating the other sensing/pacing channels in either the same or the contralateral chamber as synchronized channels for sensing/pacing one or more synchronized sites. Pacing and sensing in the rate channel then follows rate chamber timing rules, while pacing and sensing in the synchronized channels follows synchronized chamber timing rules as described above. The same or different synchronized pacing modes may be used in each synchronized channel.

4. Ventricular Rate Regularization

Ventricular rate regularization (VRR) is a ventricular pacing mode in which the LRL of the pacemaker is dynamically adjusted in accordance with a detected intrinsic ventricular rate. When a pacemaker is operating in a ventricular pacing mode (e.g., VVI or DDD), intrinsic ventricular beats occur when the instantaneous intrinsic rate rises above the LRL of the pacemaker. Thus, paces are interspersed with intrinsic beats, and the overall ventricular rhythm as a result of both paces and intrinsic beats is determined by the LRL and the mean value and variability of the intrinsic ventricular rate. VRR regularizes the overall ventricular rhythm by adjusting the LRL of the pacemaker in accordance with changes in the measured intrinsic rate.

5. Pace Counter Isolation

Resynchronization therapy is only as effective as to the extent to which paces are delivered and not inhibited by intrinsic activity. In order to provide a clinician with diagnostic information enabling proper adjustment of pacing parameters to optimally deliver cardiac resynchronization therapy, data needs to be collected by the pacemaker which reflects the events responsible for causing paces to be delivered or inhibited over a period of time. In accordance with the present invention, isolated pace counters are provided for separately counting different pacing events in each pacing channel. Depending upon the pacing mode which is being used, separate counters are provided for separately counting paces due to expiration of different escape intervals and triggering events. In a ventricular resynchronization pacing mode, for example, counters are provided for separately counting paces delivered to rate ventricular rate chamber due to expiration of a ventricular escape interval corresponding to the lower rate limit setting and due to expiration of the atrio-ventricular interval in an atrial tracking mode. Separate counters are also provided to count paces delivered to the rate and/or synchronized ventricles that are triggered by ventricular senses in a ventricular triggered mode. Separate counts of senses from each sensing channel may be also maintained.

FIGS. 2 through 5 illustrate examples of how the separate pace counters can be used for diagnostic purposes in order to optimally deliver ventricular resynchronization therapy. Each figure shows the sense and pace counts as they would be collected by non-separated counters, and the same data as reflected by isolated counters in accordance with the invention. The counts are shown for sensing and pacing events in each ventricular sensing/pacing channel. In all cases, the counts are presented as a percentage of total cardiac cycles.

FIG. 2 shows exemplary counts collected by a pacemaker operating in an atrial tracking mode with one ventricular sensing/pacing channel. It is desirable in such a situation that ventricular paces should track the atria as much as possible. The non-separated counter column shows that the ventricle is being 100% paced. However, the isolated counters reveal that the reason for the ventricular pacing is all due to expiration of the LRL escape interval. This indicates that the LRL setting is inappropriately programmed in order for the pacing rate to be controlled by intrinsic atrial activity.

FIG. 3 shows another example of data collected by a pacemaker with one sensing/pacing channel operating in an atrial tracking mode. The non-separated counters indicate that the ventricles are being 100% paced, which is what is desired in ventricular resynchronization pacing. However, the separated pace counters reveal that many of the ventricular paces are not occurring at the expiration of the atrio-ventricular interval indicating too high an atrial rate, the effect of VRR, or other condition interfering with proper AV sequential pacing.

FIG. 4 shows data collected by a pacemaker with right and left ventricular sensing channels operating in a left ventricular-only pacing mode that includes ventricular rate regularization and biventricular triggering. FIG. 5 shows the same data as in FIG. 4, but presented to show the total pace counts due to all events for each ventricular channel and separate counts for each type of pacing event expressed as a percentage of the total paces in that channel. In this example, what is desired is left ventricular pacing due to expiration of the LRL ventricular escape interval. The non-separated counters show that the left ventricle is paced frequently, but not at the ideal of 100%. Also, the percentage of right ventricular paces is quite high, and it is clear that this is due to frequent left ventricular senses occurring (i.e., right ventricular safety paces are being delivered). The separated counters help to diagnose the situation. The right ventricular counters reveal that there has been a right ventricular safety pace on 25% of the cycles which indicated oversensing of the left ventricle. The right ventricular counters also show that 60% of the cycles were triggered right ventricular paces, while the left ventricular counters show that only 45% of the cycles had a triggered left ventricular pace. This further indicates a left ventricular oversensing situation. Finally, it can be seen that only 15% of the cycles were of the type desired, a left ventricular pace due to expiration of the LRL escape interval.

The above-described embodiments dealt with ventricular resynchronization pacing modes in which the right and left ventricles were designated as the rate and synchronized chambers, respectively. Embodiments may similarly be constructed in which contralateral heart chambers are designated as the rate and synchronized chambers or in which a plurality of synchronized channels are utilized to provide synchronized pacing to multiple sites of a single chamber. In each of these cases, separate counters may be maintained for each sensing/pacing channel.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management system, comprising:
   means for sensing depolarizations in at least one heart chamber and generating a sense when depolarization occurs in a heart chamber;
   means for delivering paces to at least one heart chamber, wherein a heart chamber is paced in accordance with a pacing mode in which a pace is delivered upon expiration of an escape interval or as a result of a triggering event; and,
   means for separately counting the number of senses received from each sensed heart chamber, the number of paces delivered to each paced heart chamber by reason of expiration of an escape interval, and the number of paces delivered to each paced heart chamber as a result of a triggering event.

2. The system of claim 1 further comprising:
   means for sensing and pacing a first ventricle, wherein the escape interval is reset by a first ventricular sense and corresponds to a lower rate limit; and,
   means for counting the number of paces delivered to the first ventricle as a result of expiration of the escape interval.

3. The system of claim 2 further comprising:
   means for pacing a second ventricle at a pacing instant defined with respect to expiration of the escape interval by a specified offset interval; and,
   means for counting the number of paces delivered to the second ventricle as a result of expiration of the escape interval.

4. The system of claim 2 further comprising means for adjusting the escape interval in order to implement ventricular rate regularization.

5. The system of claim 1 further comprising:
   means for sensing and pacing a first ventricle, wherein the triggering event is a ventricular sense; and,
   means for counting the number of paces delivered to the first ventricle as a result of the triggering event.

6. The system of claim 1 further comprising:
   means for sensing a second ventricle, wherein the triggering event is a second ventricular sense; and,
   means for counting the number of paces delivered to the first ventricle as a result of the triggering event.

7. The system of claim 1 further comprising:
   means for sensing and pacing a first ventricle upon expiration of the escape interval;
   means for sensing a second ventricle, wherein the escape interval is reset by a second ventricular sense; and,
   means for counting the number of paces delivered to the first ventricle as a result of expiration of the escape interval.

8. The system of claim 1 further comprising:
   means for pacing and sensing a first ventricle;
   means for sensing atrial depolarizations and generating atrial senses in accordance therewith;
   means for pacing the first ventricle upon expiration of an atrio-ventricular escape interval triggered by an atrial sense and stopped by a first ventricular sense; and,
   means for separately counting the number of first ventricular paces delivered by reason of expiration of the atrio-ventricular escape interval.

9. The system of claim 8 further comprising:
   means for pacing a second ventricle at a pacing instant defined with respect to expiration of the atrio-ventricular escape interval by a specified offset interval; and,
   means for counting the number of paces delivered to the second ventricle as a result of expiration of the atrio-ventricular escape interval.

10. The system of claim 1 further comprising:
    means for pacing a first ventricle;
    means for sensing a second ventricle;
    means for sensing atrial depolarizations and generating atrial senses in accordance therewith;
    means for pacing the first ventricle upon expiration of an atrio-ventricular escape interval triggered by an atrial sense and stopped by a second ventricular sense; and,
    means for separately counting the number of first ventricular paces delivered by reason of expiration of the atrio-ventricular escape interval.

11. The system of claim 1 further comprising means for displaying separate counts for each heart chamber sense and each heart chamber pace as a percentage of total cardiac cycles.

12. The system of claim 11 further comprising means for displaying total pace counts due to all events for each paced heart chamber and separate counts for each type of pacing event expressed as a percentage of the total paces to delivered to each heart chamber.

13. A cardiac rhythm management system, comprising:
    means for sensing depolarizations in a ventricle and generating a ventricular sense when depolarization occurs in the ventricle;
    means for sensing depolarizations in an atrium and generating an atrial sense when depolarization occurs in the atrium;
    means for pacing the ventricle upon expiration of a lower rate limit escape interval which is reset by a ventricular sense;
    means for pacing the ventricle upon expiration of an atrio-ventricular escape interval which is triggered by an atrial sense and stopped by an ventricular sense; and,
    means for counting the number of ventricular paces delivered by reason of expiration of the lower limit escape interval and the number of ventricular paces delivered by reason of expiration of the atrio-ventricular escape interval.

14. The system of claim 13 further comprising means for displaying separate counts for ventricular paces delivered by reason of expiration of the lower limit escape interval and ventricular paces delivered by reason of expiration of the atrio-ventricular escape interval as a percentage of total cardiac cycles.

15. The system of claim 13 further comprising means for displaying a total ventricular pace count and separate counts for ventricular paces delivered by reason of expiration of the lower limit escape interval and ventricular paces delivered by reason of expiration of the atrio-ventricular escape interval expressed as a percentage of the total ventricular pace count.

16. The system of claim 13 further comprising means for adjusting the lower rate escape interval by ventricular rate regularization.

17. A cardiac rhythm management system, comprising:

means for sensing depolarizations in a first ventricle and generating a ventricular sense when depolarization occurs in the first ventricle;

means for sensing depolarizations in a second ventricle and generating a ventricular sense when depolarization occurs in the second ventricle;

means for pacing the second ventricle upon expiration of a lower rate limit escape interval which is reset by a first ventricular sense;

means for inhibiting a pace to the second ventricle when the lower rate limit escape interval expires during a protective period initiated by a second ventricular sense;

means for pacing the first ventricle with a safety pace upon expiration of the lower rate limit escape interval when a pace to the second ventricle is inhibited by the protective period; and, means for separately counting the number of second ventricular paces and the number of first ventricular safety paces.

18. The system of claim 17 further comprising:

means for triggering a pace to the first ventricle after a second ventricular sense;

means for triggering a pace to the second ventricle after a first ventricle sense; and, means for separately counting the number of triggered paces delivered to each ventricle.

19. The system of claim 17 further comprising:

means for sensing depolarizations in an atrium and generating an atrial sense when depolarization occurs in the atrium;

means for pacing the second ventricle upon expiration of an atrio-ventricular escape interval which is triggered by an atrial sense and stopped by a first ventricular sense; and, means for separately counting the number of second ventricular paces delivered by reason of expiration of the atrio-ventricular escape interval and the number of second ventricular paces delivered by reason of expiration of the lower limit rate escape interval.

20. The system of claim 19 further comprising:

means for inhibiting a pace to the second ventricle when the atrio-ventricular escape interval expires during a protective period initiated by a second ventricular sense; and, means for pacing the first ventricle with a safety pace upon expiration of the atrio-ventricular escape interval when a pace to the second ventricle is inhibited by the protective period.

* * * * *

UNITED STATES PATENT AND TRADEMARK OFFICE
CERTIFICATE OF CORRECTION

PATENT NO. : 7,130,688 B2
APPLICATION NO. : 10/291934
DATED : October 31, 2006
INVENTOR(S) : Stahmann et al.

Page 1 of 1

It is certified that error appears in the above-identified patent and that said Letters Patent is hereby corrected as shown below:

On the Title page, Item (75), "Inventors", delete "White Bear Lake, MN (US);" and insert -- Overijse (BE); --, therefor.

On the Title page, Item (57), "Abstract", after "method" insert -- for --.

In column 11, line 55, in Claim 6, after "comprising" delete ";" and insert -- : --, therefor.

Signed and Sealed this

First Day of May, 2007

JON W. DUDAS
*Director of the United States Patent and Trademark Office*